United States Patent [19]

Jung et al.

[11] Patent Number: 4,486,426
[45] Date of Patent: Dec. 4, 1984

[54] UNSATURATED CEPHALOSPORIN DERIVATIVES

[75] Inventors: Frederich H. Jung, Rilly la Montaque, France; Gareth M. Davies, Macclesfield, England

[73] Assignee: Imperial Chemical Industries, PLC, Hertfordshire, England

[21] Appl. No.: 399,875

[22] Filed: Jul. 19, 1982

[30] Foreign Application Priority Data

Jul. 23, 1981 [EP] European Pat. Off. ........ 81401179.7

[51] Int. Cl.³ ................. C07D 501/18; A61K 31/425
[52] U.S. Cl. .................................... 424/246; 544/21; 544/22; 544/26; 544/27; 260/245.3
[58] Field of Search ............ 544/21, 22, 26, 27, 544/25; 424/246; 542/413

[56] References Cited

U.S. PATENT DOCUMENTS 4,283,397 8/1981 Hannah .................. 544/27

FOREIGN PATENT DOCUMENTS 0018595 12/1980 European Pat. Off. .
0031708 7/1981 European Pat. Off. .
2051788 1/1981 United Kingdom .

*Primary Examiner*—Nicholas S. Rizzo
*Attorney, Agent, or Firm*—Cushman, Darby & Cushman

[57] ABSTRACT

An antibacterial cephalosporin derivative of the formula I:

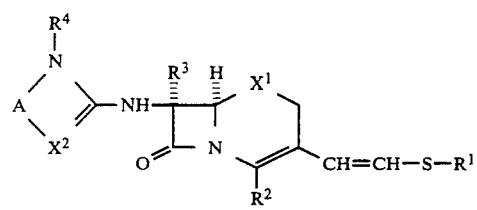

in which $X^1$ is sulphur, oxygen, sulphinyl or sulphonyl; $R^1$ is a variety of radicals defined in the specification; $R^2$ is any one of the C-4 substituents from antibacterially-active cephalosporins known in the art; $R^3$ is hydrogen or methoxy; $X^2$ is nitrogen or a radical $N \oplus R^8$; $R^4$ and $R^8$ are a variety of radicals described in the specification; —A— is of the formula V or VI:

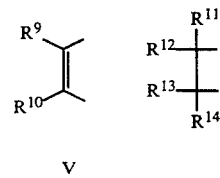

V          VI in which $R^9$, $R^{10}$, $R^{11}$, $R^{12}$, $R^{13}$ and $R^{14}$ are a variety of substituents described in the specification; and the pharmaceutically-acceptable acid- and base-addition salts thereof. Pharmaceutical compositions and manufacturing processes are also described.

6 Claims, 37 Drawing Figures

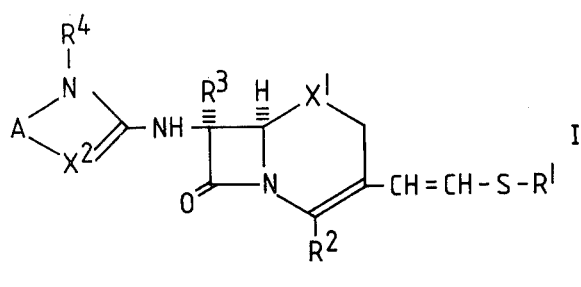 I
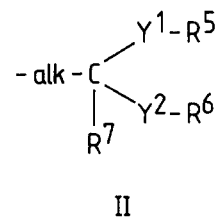 II
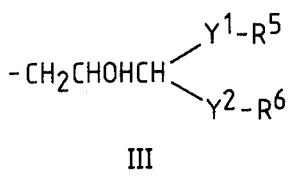
III
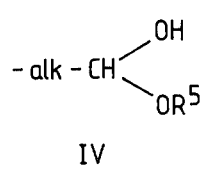
IV
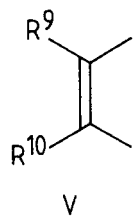
V
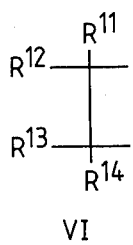
VI
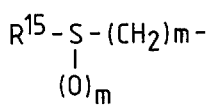
VII
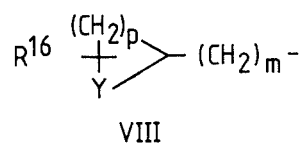
VIII
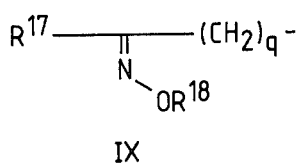
IX
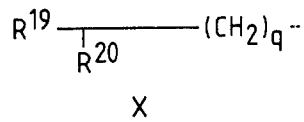
X
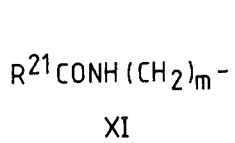
XI
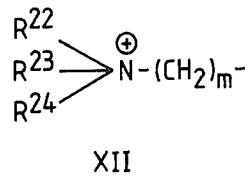
XII
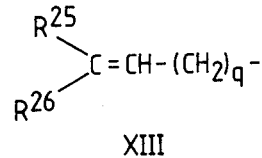
XIII

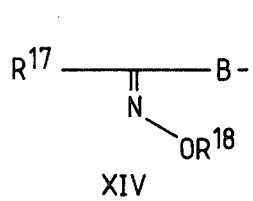
XIV
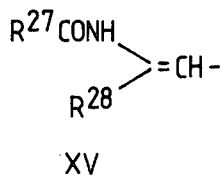
XV
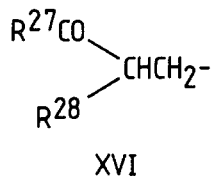
XVI
OCONH$_2$
XVII
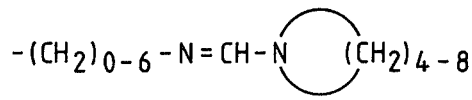
XVIII
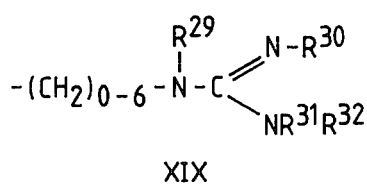
XIX
$-(CH_2)_{0-6}-NHCOCH_2NH_2$
XX
$-(CH_2)_{0-6}-NHCOCH(Ph)NH_2$
XXI
$-(CH_2)_{0-6}-NHCN$
XXII
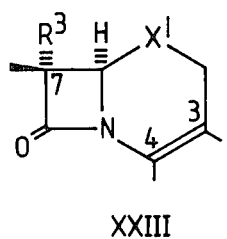
XXIII
COOCHR$^{33}$OCOR$^{34}$
XXIV
COOCHR$^{33}$SCOR$^{34}$
XXV
COOCHR$^{33}$OR$^{34}$
XXVI
COOCOOR$^{34}$
XXVII
COOCHR$^{33}$OCOR$^{34}$
XXIX

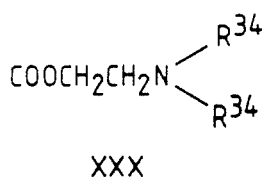
XXX
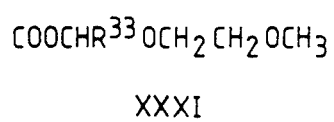
XXXI
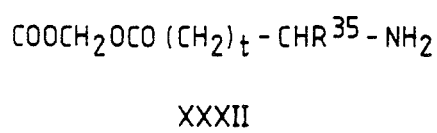
XXXII
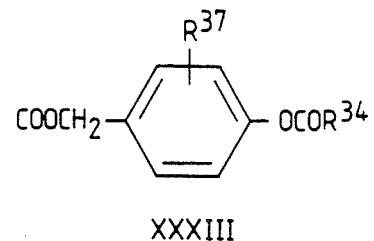
XXXIII
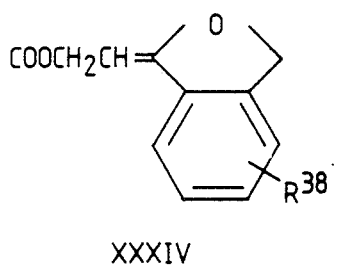
XXXIV
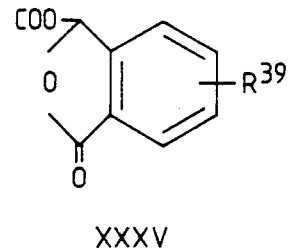
XXXV
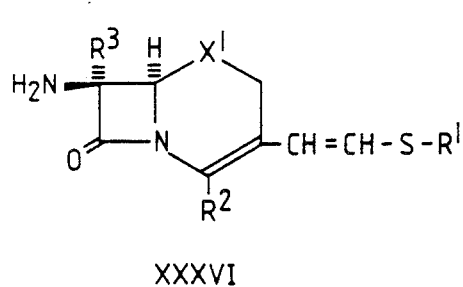
XXXVI
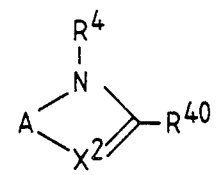
XXXVII

UNSATURATED CEPHALOSPORIN DERIVATIVES

This invention relates to cephalosporin derivatives which have antibacterial properties.

The vast majority of therapeutically useful antibiotics based on the penicillin and cephalosporin ring systems have an acylamino radical at the 6β and 7β positions respectively. A number of other substituents at these positions have been investigated but in the main the resulting compounds have at best possessed only weak antibacterial activity. One exception to this generalisation is the amidino substituent. Penicillin derivatives carrying a substituted amidino radical in the 6β position (see for example UK Pat. Nos. 1,315,566 and 1,406,732) have been found to have useful antibacterial activity and two such compounds, mecillinam and pivmecillinam, are commercially available. However, the corresponding cephalosporin derivatives have been found to have a surprisingly low level of antibacterial activity. European Patent Publication No. 18595 describes a series of cephalosporin derivatives carrying a 2- or 4-pyridinioamino radical in the 7-position.

European Patent Publications Nos. 31708 and 55562 describe cephalosporin derivatives carrying an imidazolin-2-ylamino or imidazol-2-ylamino radical in the 7-position and a known substituent in the 3-position of the cephalosporin nucleus. The present application represents an extension of this work to a new range of substituents in the 3-position.

According to the invention there is provided a cephalosporin derivative of the formula I:

[Formula I given hereafter]

in which $X^1$ is sulphur, oxygen, sulphinyl or sulphonyl; $R^1$ is (1) 1–6C alkyl (e.g. methyl), L-2-amino-2-carboxyethyl or phenyl;

(2) pyridyl or the N-oxide thereof;

(3) pyridazin-3-yl substituted in the 6-position by 1–6C alkyl (e.g. methyl), methoxy, amino or 1–6C acylamino (e.g. acetylamino), or the N-oxide thereof, or pyrimidin-2-yl or tetrazolo[4,5-b]pyridazin-6-yl;

(4) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl in which the alkoxycarbonyl is 2–6C (e.g. methoxycarbonyl), each substituted in the 1-position:

(a) by 1–6C alkyl (e.g. methyl), optionally substituted by 1–6C alkoxy (e.g. methoxy), 1–6C alkylthio (e.g. methylthio), phenyl, formyl, carbamoyl, 2–6C alkylcarbamoyl (e.g. methylcarbamoyl), 3–10C dialkylcarbamoyl (e.g. dimethylcarbamoyl), 1–6C alkanoyl (e.g. acetyl), 2–6C alkoxycarbonyl (e.g. methoxycarbonyl) or thiazolidin-2-yl;

(b) by allyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxyprop-2-yl;

(c) by 2–4C alkyl (e.g. ethyl) substituted by hydroxy, carbamoyloxy, 1–6C alkanoyl (e.g. acetyl) (which can itself be optionally substituted by amino, 1–6C alkylamino [e.g. methylamino] or 2–10C dialkylamino [e.g. dimethylamino]), 1–6C alkanesulphinyl (e.g. methanesulphinyl), 1–6C alkanesulphonyl (e.g. methanesulphonyl), amino, 1–6C alkylamino (e.g. methylamino), 2–10C dialkylamino (e.g. dimethylamino), sulphoamino, 1–6C alkanesulphonylamino (e.g. methanesulphonylamino), sulphamoylamino, 1–6C alkanoylamino (e.g. acetylamino) (which can itself be optionally substituted by hydroxy, amino, 1–6C alkylamino [e.g. methylamino] or 2–10C dialkylamino [e.g. dimethylamino]), 2–6C alkoxycarbonylamino (e.g. methoxycarbonylamino), ureido, 2–6C alkylureido (e.g. methylureido), or 3–10C dialkylureido (e.g. dimethylureido);

(d) by a radical of the formula II, III or IV:

[Formula II]

[Formula III]

[Formula IV]

in which alk is 1–4C alkylene (e.g. methylene), $Y^1$ and $Y^2$ are the same and are oxygen or sulphur and $R^5$ and $R^6$ are the same and are 1–6C alkyl (e.g. methyl), or $Y^1$ and $Y^2$ are the same or different and are oxygen or sulphur and $R^5$ and $R^6$ are joined to form 2–3C alkylene (e.g. ethylene), and $R^7$ is hydrogen or 1–3C alkyl (e.g. methyl);

(e) by 1–6C alkyl (e.g. methyl) substituted by 1–6C alkoxyimino (e.g. methoxyimino) or hydroxyimino;

(5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl in each of which the alkyl is 1–6C (e.g. methyl);

(6) 1,3,4-triazol-5-yl, 1,2,3-triazol-5-yl or 1-alkyl-1,2,4-triazol-5-yl in which the alkyl is 1–6C (e.g. methyl) which is optionally substituted in the 3-position by 2–6C alkoxycarbonyl (e.g. methoxycarbonyl);

(7)a. 1,3,4-thiadiazol-5-yl optionally substituted by 1–6C alkyl (e.g. methyl), trifluoromethyl, 1–6C alkoxy (e.g. methoxy), 1–6C alkylthio (e.g. methylthio), 2–4C hydroxyalkylthio (e.g. 2-hydroxyethylthio), 1–6C alkanesulphonyl (e.g. methanesulphonyl), hydroxy, 1–6C hydroxyalkyl (e.g. hydroxymethyl), carboxy, 2–6C carboxyalkyl (e.g. carboxymethyl), amino, 1–6C alkylamino (e.g. methylamino), 2–10C dialkylamino (e.g. dimethylamino), 1–6C aminoalkyl (e.g. aminomethyl), 2–8C alkylaminoalkyl (e.g. methylaminomethyl), 3–12C dialkylaminoalkyl (e.g. dimethylaminomethyl), 1–6C alkanoylamino (e.g. acetylamino) or 2–8C alkanoylaminoalkyl (e.g. acetylaminomethyl), or b. 1,2,4-thiadiazol-5-yl substituted by 1–6C alkyl (e.g. methyl) or 1–6C alkoxy (e.g. methoxy);

(8)a. 1,3,4-oxadiazol-5-yl optionally substituted by 1–6C alkyl (e.g. methyl), trifluoromethyl, phenyl, 1–6C aminoalkyl (e.g. aminomethyl), 2–8C alkylaminoalkyl (e.g. methylaminomethyl), 3–10C dialkylaminoalkyl (e.g. dimethylaminomethyl) or 2–8C alkanoylaminoalkyl (e.g. acetylaminomethyl) or b. oxazol-2-yl optionally substituted in the 4-position by 1–6C alkyl (e.g. methyl);

(9) tetrazol-5-yl optionally substituted in the 1-position by:

(a) 1–6C alkyl (e.g. methyl) itself optionally substituted by 1–6C alkoxy (e.g. methoxy), sulpho, carboxy, formyl or sulphamoyl;

(b) 2–4C alkyl (e.g. ethyl) substituted by hydroxy, amino, 1–6C alkylamino (e.g. methylamino), 2–8C dialkylamino (e.g. dimethylamino), 1–6C alkanoylamino (e.g. acetylamino), 2–6C carboxyalkylamino (e.g. carboxymethylamino), sulphamoylamino, sulphoamino, ureido, 2–6C alkylureido (e.g. methylureido) or 3–8C dialkylureido (e.g. dimethylureido);

(c) 1–5C alkyl (e.g. methyl) substituted by hydroxyimino or 1–6C alkoxyimino (e.g. methoxyimino);

(d) phenyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxy-2-propyl; or (e) a radical of the formula II above in which $R^7$ is hydrogen, or a radical of the formula III above, in both of which $Y^1$, $Y^2$, $R^5$ and $R^6$ are as given above; $R^2$ is any one of the C-4 substituents from antibacterially-active cephalosporins known in the art; $R^3$ is hydrogen or methoxy; $X_2$ is nitrogen or $N^{\oplus}R^8$; $R^4$ and $R^8$, which may be the same or different, are hydrogen, 1–6C alkyl (e.g. methyl), hydroxy, 1–6C alkoxy (e.g. methoxy), amino, 1–6C alkanoylamino (e.g. acetylamino), 1–6C alkylamino (e.g. methylamino), 1–6C aminoalkyl (e.g. 2-aminoethyl), 2–6C hydroxyalkyl (e.g. 2-hydroxyethyl), 2–6C carboxyalkyl (e.g. 2-carboxyethyl), 2–6C alkenyl (e.g. allyl), 3–6C alkoxyalkyl (e.g. methoxymethyl), 3–8C alkoxycarbonylalkyl (e.g. methoxycarbonylmethyl), furylmethyl, phenyl or 7–11C phenylalkyl (e.g. benzyl), in the latter two of which the phenyl ring is optionally substituted by halogen (e.g. F, Cl, Br), methyl, methoxy, nitro, hydroxy, amino, carboxy or methoxycarbonyl; —A— is a radical of the formula V or VI:

[Formula V]

[Formula VI]

in which $R^9$ and $R^{10}$, which may be the same or different, are 1–6C haloalkyl, 1–6C azidoalkyl, 2–6C cyanoalkyl, 2–6C carboxyalkyl, 3–8C alkoxycarbonylalkyl, 2–6C carbamoylalkyl, 3–8C alkylcarbamoylalkyl, 4–10C dialkylcarbamoylalkyl, 2–6C (amino)(carboxy)-alkyl, 2–6C alkenyl, 2–6C nitroalkenyl, 8–15C arylalkenyl, 14–25C diarylalkenyl, 20–35C triarylalkenyl, 1–6C alkylthio, 2–6C aminoalkylthio, 3–8C alkylaminoalkylthio, 4–12C dialkylaminoalkylthio, 2–6C aminoalkoxy, 3–8C alkylaminoalkoxy, 4–12C dialkylaminoalkoxy, 6–10C arylthio, 6–10C aryloxy, 7–11C arylalkyl, amino, 1–6C alkylamino, 2–8C dialkylamino, 6–10C arylamino, 7–11C arylalkylamino, 12–20C diarylamino, 1–6C alkanoyl, 7–11C aroyl, 2–6C alkoxycarbonylamino, 7–11C aryloxycarbonylamino, 2–6C alkoxythiocarbonylamino, 7–11C aryloxythiocarbonylamino, 2–6C alkoxythiocarbonylamino, 7–11C aryloxythiocarbonylamino, 1–6C alkanoylamino, 7–11C aroylamino, 2–6C alkylureido, 7–11C arylureido, 3–8C hydroxyalkenyl, carbamoyl, 2–6C alkylcarbamoyl, 3–8C dialkylcarbamoyl, 5–10C (dialkylaminoalkyl)carbamoyl, 7–11C arylcarbamoyl, thiocarbamoyl, 2–6C (alkyl)thiocarbamoyl, 3–8C (dialkyl)-thiocarbamoyl, 7–11C (aryl)thiocarbamoyl, 5–10C (dialkylaminoalkyl)thiocarbamoyl, 2–6C alkoxyalkyl, 2–6C alkanoyloxyalkyl, 2–6C carbamoyloxyalkyl, 3–8C alkylcarbamoyloxyalkyl, 4–12C dialkylcarbamoyloxyalkyl, 7–11C (aryl)(hydroxy)alkyl, 7–11C (aryl) (amino)alkyl, 2–6C alkanoylaminoalkyl, 3–8C haloalkanoylaminoalkyl, 8–15C aroylaminoalkyl, 2–6C ureidoalkyl, 3–8C (alkylureido)alkyl, 4–12C (dialkylureido)alkyl, 8–15C (arylureido)alkyl, guanidinoalkyl, 2–6C formimidoylaminoalkyl, 3–8C alkylimidoylaminoalkyl, 1–6C alkoxy, 2–6C formylalkyl, 2–10C alkanesulphonylaminoalkyl, 7–15C arenesulphonylaminoalkyl, 2–6C alkyl substituted on different carbons by two radicals selected from hydroxy, nitro, amino, 1–6C alkylamino, 2–8C dialkylamino, 6–10C arylamino, 7–11C arylalkylamino, 7–15C (aryl)(alkyl)amino, 8–20C (arylalkyl)-(alkyl)amino, pyrrolidino, piperidino, piperazino, N-methylpiperazino, morpholino, 1–6C alkoxy, 1–6C alkylthio, 6–10C aryloxy, 6–10C arylthio, 7–11C arylalkoxy and 7–11C arylalkylthio, 2–6C alkyl substituted on one carbon by nitro, amino, 1–6C alkylamino, 2–10C dialkylamino or 1–6C alkanoylamino and on a different carbon by methyl which is itself substituted by two radicals selected from cyano, 2–6C alkoxycarbonyl and 1–6C alkanoyl, radicals of the formula VII, VIII, IX, X, XI, XII or XIII:

[Formula VII]

[Formula VIII]

[Formula IX]

[Formula X]

[Formula XI]

[Formula XII]

[Formula XIII]

in which Y is oxygen, sulphur or $CH_2$, m is 1 to 6, q is 0 to 6, n is 0 to 2, p is 1 to 4, $R^{15}$ is 1–6C, alkyl, 6–10C aryl or 7–11C aralkyl, $R^{16}$ is hydrogen, 1–6C alkyl or 6–10C aryl, $R^{17}$ is hydrogen, 1–6C alkyl, 6–10C aryl, 7–11C arylalkyl or heterocyclyl, $R^{18}$ is hydrogen or 1–6C alkyl which is optionally substituted by carboxy, 2–6C alkoxycarbonyl, carbamoyl or cyano, $R^{19}$ is heterocyclyl, $R^{20}$ is hydroxy or amino, $R^{21}$ is pyridyl, $R^{22}$, $R^{23}$ and $R^{24}$, which may be the same or different, are hydrogen, 1–6C alkyl or 6–10C aryl and $R^{25}$ and $R^{26}$, which may be the same or different, are cyano, nitro, 2–6C alkoxycarbonyl, 7–11C aryloxycarbonyl, 1–6C alkanoyl or 7–11C aroyl, or $R^9$ and $R^{10}$ are heterocyclic radicals which are linked (to the imidazole ring) by a direct bond or by a methylene or thiomethylene ($SCH_2$) bridge, or $R^9$ and $R^{10}$ are hydrogen, halogen, 1–6C alkyl, cyano, hydroxy, carboxy, 2–6C alkoxycarbonyl, 1–6C aminoalkyl, 2–10C alkylaminoalkyl, 3–15C dialkylaminoalkyl or 1–6C hydroxyalkyl, or phenyl optionally substituted by 1 or 2 radicals selected from halogen, nitro, amino, hydroxy, carboxy, cyano, 1–6C alkyl and 2–6C alkoxycarbonyl, or $R^9$ and $R^{10}$ are 1–6C nitroalkyl, 4–8C alkadienyl, 4–8C alkenynyl, 3–10C alkoxycarbonylaminoalkyl, 3–10C alkylcarbamoylalkyl, 4–15C dialkylcarbamoylalkyl, 8–15C arylcarbamoylalkyl, 3–15C heterocyclylcarbonylaminoalkyl, 4–15C heterocyclylalkylcarbonylaminoalkyl, 3–10C alkanoylcarbamoyloxyalkyl, 9–18C aroylcarbamoyloxyalkyl, 4–15C heterocyclylcarbonylcarbamoyloxyalkyl, 8–18C arylcarbamoyloxyalkyl, 3–15C heterocyclylcarbamoyloxyalkyl, 3–10C (haloalkylureido)alkyl, 8–18C (arylureido)alkyl, 3–15C (heterocyclylureido)alkyl, 3–10C [alkyl(thioureido)]alkyl, 3–10C [haloalkyl(thioureido)]-alkyl, 8–18C [aryl(thioureido)]alkyl, 3–15C [heterocyclyl(thioureido)]alkyl, 1-aminocyanomethyl, 1-dimethylaminocyanomethyl or N-trifluoroacetyl-N-benzylaminomethyl or radicals of the formula XIV, XV or XVI:

[Formula XIV]

[Formula XV]

[Formula XVI]

in which $R^{17}$ and $R^{18}$ have the meanings given above, B is 2–6C alkenylene, $R^{27}$ is hydrogen, 1–6C alkyl, 6–10C aryl or 4–7C cycloalkyl and $R^{28}$ is carboxy, carbamoyl, 2–6C alkoxycarbonyl or toluene-p-sulphonyl, wherein when $R^9$ or $R^{10}$ contains an aryl radical, that aryl radical may optionally be substituted by 1 or 2 substituents selected from halogen, nitro, amino, hydroxy, carboxy, cyano, 1–6C alkyl, 2–6C alkoxycarbonyl, sulpho, 1–6C alkoxy, 1–6C haloalkyl, 1–6C alkylsulphamoyl, 2–8C dialkylsulphamoyl and 2–8C dialkylamino, and wherein when $R^9$ or $R^{10}$ contains a heterocyclic radical that radical is a 5- or 6-membered aromatic or non-aromatic heterocyclic radical which contains 1, 2, 3 or 4 hetero atoms selected from oxygen, nitrogen and sulphur, such ring, where possible, optionally being in the form of the N-oxide and such ring being optionally fused with a benzene ring, and such fused benzene ring and/or (where possible) the heterocyclic ring being optionally substituted by one or two substituents selected from halogen, 1–6C alkyl, hydroxy, 1–6C alkoxy, phenoxy, mercapto, 1–6C alkylthio, phenylthio, carboxy, 2–6C alkoxycarbonyl, phenoxycarbonyl, carbamoyl, 2–6C alkylcarbamoyl, 3–10C dialkylcarbamoyl, phenylcarbamoyl, diphenylcarbamoyl, nitro, amino, 1–6C alkylamino, 2–8C dialkylamino, phenylamino, 7–12C (phenyl)(alkyl)amino, diphenylamino, carboxyamino, 2–6C (carboxy) (alkyl)amino, (carboxy) (phenyl)amino, 1–6C alkanoylamino, 2–10C (alkanoyl) (alkyl)amino, benzoylamino, 8–14C (benzoyl) (alkyl)amino, cyano, phenyl, sulphamoyl, 1–6C alkylsulphamoyl, 2–10C dialkylsulphamoyl, phenylsulphamoyl, 1–6C haloalkyl, 1–6C aminoalkyl, 2–8C alkylaminoalkyl, 3–12C dialkylaminoalkyl, 2–6C carboxyalkyl, 1–6C sulphoalkyl and oxo; or $R^{10}$ and $R^9$ are joined to form, together with the carbon atoms to which they are attached, a mono-, bi- or tri-cyclic carbocyclic ring system which may be non-aromatic, partially aromatic or fully aromatic, the aromatic part of such a ring system being optionally substituted by 1, 2 or 3 radicals selected from halogen, hydroxy, amino, cyano, carboxy, carbamoyl, nitro, ureido, 1–6C alkyl, 1–6C alkoxy, 1–6C haloalkyl, 1–6C alkylamino, 1–6C hydroxyalkyl, 1–6C aminoalkyl, 1–6C alkanoylamino, 1–6C azidoalkyl, 2–8C dialkylamino, 2–10C alkylaminoalkyl, 3–15C dialkylaminoalkyl, 2–6C cyanoalkyl, 2–6C carboxyalkyl, 2–6C carbamoylalkyl and 2–6C ureidoalkyl and radicals of the formula XVII, XVIII, XIX, XX, XXI and XXII:

[Formula XVII]

[Formula XVIII]

[Formula XIX]

[Formula XX]

[Formula XXI]

[Formula XXII]

in which $R^{29}$, $R^{30}$, $R^{31}$ and $R^{32}$, which may be the same or different, are hydrogen or 1–6C alkyl; and $R^{11}$, $R^{12}$, $R^{13}$ and $R^{14}$, which may be the same or different, are hydrogen, carboxy, cyano, pyridyl, 1–6C alkanoyl, 1–6C hydroxyalkyl, 1–10C alkyl, 7–12C phenoxyalkyl in which the phenyl ring is optionally substituted by diphenylmethyl, or phenyl which is optionally substituted by 1, 2 or 3 radicals selected from halogen, cyano, amino, carboxy, carbamoyl, hydroxy, phenyl, phenoxy, diphenylmethyl, 1–6C alkylamino, 1–6C alkanoylamino, 1–6C alkanesulphonylamino, 1–6C aminoalkyl, 1–6C hydroxyalkyl, 2–10C dialkylamino, 2–6C alkoxycarbonyl, 2–6C alkylcarbamoyl and 3–10C dialkylcarbamoyl; or $R^{12}$ and $R^{13}$, when in the cis relationship, are joined to form, together with the carbons to which they are attached, a 3 to 6 membered carbocyclic ring, the ring being optionally substituted by 1 or 2 radicals selected from phenyl and 1–6C haloalkyl and the 4 to 6 membered rings optionally containing a double bond in a position other than at the ring fusion; provided that when one of $R^{11}$, $R^{12}$, $R^{13}$ and $R^{14}$ is carboxy the remaining members of $R^{11}$, $R^{12}$, $R^{13}$ and $R^{14}$ are hydrogen: and where the compound of the formula I contains a free basic or acidic group, the pharmaceutically-acceptable acid- or base-addition salts respectively thereof.

It is to be understood that in the above formula I and thoughout this specification, the illustrated stereochemistry of the ceph-3-em nucleus of the formula XXIII:

[Formula XXIII]

is the absolute configuration. It is also to be understood that although the double bond or bonds in the ring attached to the 7-amino group has or have been inserted in particular positions, other tautomeric forms are, in certain instances, possible. Note, however, that the delta-3 double bond is fixed in position. The double bond to which $R^1$ is attached may be in the cis or trans configuration, or a mixture of these. When the compound of the formula I contains both an acidic and a basic centre, the compound may exist in the form of a zwitterion.

A particular value for $R^2$ is carboxy, tetrazol-5-yl or a radical of the formula XXIV, XXV, XXVI, XXVII, XXVIII, XXIX, XXX, XXXI, XXXII, XXXIII, XXXIV or XXXV:

[Formula XXIV]

[Formula XXV]

[Formula XXVI]

[Formula XXVII]

[Formula XXVIII]

[Formula XXIX]

[Formula XXX]

[Formula XXXI]

[Formula XXXII]

[Formula XXXIII]

[Formula XXXIV]

[Formula XXXV]

in which $R^{33}$ is hydrogen or 1–6C alkyl, $R^{34}$ is 1–6C alkyl, $R^{35}$ is hydrogen, 1–6C alkyl, 7–11C arylalkyl or 2–6C alkoxycarbonyl, t is 0 or 1, $R^{36}$ is 1–6C alkyl, 6–10C aryl or 7–11C aralkyl, $R^{37}$ is hydrogen or one, two or three radicals selected from halogen, nitro, cyano, 1–6C alkyl, 1–6C alkoxy, 1–6C alkylthio, 1–6C alkylsulphinyl, 1–6C alkanesulphonyl, 2–6C alkoxycarbonyl, 2–6C alkoxythiocarbonyl, 2–6C alkanoylamino, 6–10C aryl, 6–10C aryloxy, 6–10C arylthio, arylsulphinyl, 6–10C arylsulphonyl, 7–11C aryloxycarbonyl, 7–11C arylthiocarbonyl and 7–11C aryloxythiocarbonyl, $R^{38}$ is hydrogen or one of the values for $R^{36}$ given above and $R^{39}$ is hydrogen or one, two or three radicals selected from halogen, 1–6C alkyl and 1–6C alkoxy.

Particular values for $R^9$ and $R^{10}$, which may be the same or different are fluoromethyl, chloromethyl, bromomethyl, difluoromethyl, trifluoromethyl, azidomethyl, 3-azidopropyl, cyanomethyl, 2-cyanoethyl, carboxymethyl, 2-carboxyethyl, methoxycarbonylmethyl, carbamoylmethyl, 2-carbamoylethyl, methylcarbamoylmethyl, dimethylcarbamoylmethyl, 2-amino-2-carboxyethyl, vinyl, allyl, 2-nitrovinyl, 2-phenylvinyl, 1-phenylvinyl, 2-phenylallyl, 3-phenylallyl, 1,2-diphenylvinyl, 2,2-diphenylvinyl, 2,3-diphenylallyl, 3,3-diphenylallyl, 1,2,2-triphenylvinyl, 2,3,3-triphenylallyl, methylthio, 2-aminoethylthio, 2-methylaminoethylthio, 2-dimethylaminoethylthio, 2-aminoethoxy, 2-methylaminoethoxy, 2-dimethylaminoethoxy, phenylthio, phenoxy, benzyl, amino, methylamino, dimethylamino, phenylamino, benzylamino, diphenylamino, formyl, acetyl, benzoyl, methoxycarbonylamino, phenoxycarbonylamino, methoxythiocarbonylamino, phenoxythiocarbonylamino, acetylamino, propionylamino, benzolyamino, 3-methylureido, 3-phenylureido, 3-hydroxyprop-1-enyl, carbamoyl, methylcarbamoyl, dimethylcarbamoyl, 2-dimethylaminoethylcarbamoyl, 3-dimethylaminopropylcarbamoyl, phenylcarbamoyl, thiocarbamoyl, (methyl)thiocarbamoyl, (dimethyl)thiocarbamoyl, (phenyl)thiocarbamoyl, (2-dimethylaminoethyl)thiocarbamoyl, methoxymethyl, 3-methoxypropyl, acetoxymethyl, 3-acetoxypropyl, carbamoyloxymethyl, methylcarbamoyloxymethyl, 3-(methylcarbamoyloxy)propyl, dimethylcarbamoyloxymethyl, (phenyl) (hydroxy)methyl, (phenyl) (amino)methyl, acetylaminomethyl, 2-acetylaminoethyl, 3-acetylaminopropyl, 2-trifluoroacetylaminoethyl, 3-trifluoroacetylaminopropyl, benzoylaminomethyl, ureidomethyl, 3-ureidopropyl, (3-methylureido)methyl, 2-(3-methylureido)ethyl, (3,3-dimethylureido)methyl, (3-phenylureido)methyl, guanidinomethyl, formimidoylaminomethyl, methylimidoylaminomethyl, methoxy, formylmethyl, methanesulphonylaminomethyl, 2-(methanesulphonylamino)ethyl, 3-(methanesulphonylamio)propyl or benzenesulphonylaminomethyl, or ethyl or propyl which are substituted on different carbons by two radicals selected from hydroxy, nitro, amino, methylamino, dimethylamino, phenylamino, benzylamino, (phenyl) (methyl)amino, (benzyl) (methyl)amino, pyrrolidino, piperidino, piperazino, N-methylpiperazino, morpholino, methoxy, methylthio, phenoxy, phenylthio, benzyloxy and benzylthio, or ethyl or propyl which are substituted on one carbon by nitro, amino, methylamino, dimethylamino or acetylamino and on a different carbon by methyl which is itself substituted by two radicals selected from cyano, methoxycarbonyl and acetyl, or $R^9$ and $R^{10}$ are radicals of the formulae VII, VIII, IX, X, XI, XII or XIII given above in which Y is oxygen, sulphur or $CH_2$, m is 1, 2 or 3, q is 0, 1 or 2, n is 0, 1 or 2, p is 1 to 4, $R^{15}$ is methyl, ethyl, phenyl or benzyl, $R^{16}$ is hydrogen, methyl or phenyl, $R^{17}$ is hydrogen, methyl, phenyl, benzyl or heterocyclyl, $R^{18}$ is hydrogen, or methyl or n-propyl optionally substituted by carboxy, methoxycarbonyl, carbamoyl or cyano, $R^{19}$ is heterocyclyl, $R^{20}$ is hydroxy or amino, $R^{21}$ is pyridyl, $R^{22}$, $R^{23}$ and $R^{24}$, which may be the same or different, are hydrogen, methyl or phenyl, and $R^{25}$ and $R^{26}$, which may be the same or different, are cyano, nitro, methoxycarbonyl, phenoxycarbonyl, acetyl or benzoyl, or heterocyclic radicals which are linked (to the imidazole ring) by a direct bond or by a methylene or thiomethylene ($SCH_2$) bridge, or hydrogen, fluorine, chlorine, bromine, methyl, cyano, hydroxy, carboxy, methoxycarbonyl, aminomethyl, 2-aminoethyl, methylaminomethyl, dimethylaminomethyl, hydroxymethyl or 2-hydroxyethyl, or phenyl optionally substituted by 1 or 2 radicals selected from fluorine, chlorine, bromine, nitro, amino, hydroxy, carboxy, cyano, methyl and methoxycarbonyl, or 2-nitroethyl, buta-1,4-dienyl, but-1-en-4-ynyl, 2-ethoxycarbonylaminoethyl, 3-isobutoxycarbonylaminopropyl, 2-methylcarbamoylethyl, 2-dimethylcarbamoylethyl, 2-phenylcarbamoylethyl, 2-heterocyclylcarbonylaminoethyl, 3-heterocyclylcarbonylaminopropyl, 3-acetylcarbamoyloxypropyl, 3-benzoylcarbamoyloxypropyl, 3-heterocyclylcarbonylcarbamoyloxypropyl, 3-phenylcarbamoyloxypropyl, 3-heterocyclylcarbamoyloxypropyl, 3-[3-(2,2,2-trifluoroethyl)ureido]propyl, 3-(3-phenylureido)propyl, 2-(3-heterocyclylureido)ethyl, 2-(3-(methyl)thioureido]ethyl, 3-[3-(2,2,2-trifluoroethyl)thioureido]propyl, 2-[3-(phenyl)thioureido]ethyl, 2-[3-(heterocyclyl)thioureido]ethyl, 1-aminocyanomethyl, 1-dimethylaminocyanomethyl or N-trifluoroacetyl-N-benzylaminomethyl or radicals of the formula XIV, XV or XVI given above in which $R^{17}$ and $R^{18}$ have the meanings given above, B is vinylene, $R^{27}$ is hydrogen, methyl, phenyl or cyclohexyl and $R^{28}$ is carboxy, carbamoyl, methoxycarbonyl or toluene-p-sulphonyl, wherein when $R^9$ or $R^{10}$ contains a phenyl radical, that phenyl may optionally be substituted by 1 or 2 substituents selected from fluorine, chlorine, bromine, nitro, amino, hydroxy, carboxy, cyano, methyl, methoxycarbonyl, sulpho, methoxy, trifluoromethyl, methylsulphamoyl, dimethylsulphamoyl and dimethylamino, and wherein, when $R^9$ or $R^{10}$ contains a heterocyclic radical, that radical is furan, thiophene, pyrrole, oxazole, thiazole, imidazole, isoxazole, isothiazole, thiadiazole, oxadiazole, triazole, tetrazole, pyridine, pyrimidine, pyrazine, pyridazine or piperazine, such ring, where possible, optionally being in the form of the N-oxide, such ring being optionally fused with a benzene ring and such fused benzene ring and/or (where possible) heterocyclic ring being optionally substituted by one or two substituents selected from fluorine, chlorine, bromine, methyl, ethyl, hydroxy, methoxy, phenoxy, mercapto, methylthio, phenylthio, carboxy, methoxycarbonyl, phenoxycarbonyl, carbamoyl, methylcarbamoyl, dimethylcarbamoyl, phenylcarbamoyl, diphenylcarbamoyl, nitro, amino, methylamino, dimethylamino, phenylamino, (phenyl) (methyl)amino, diphenylamino, carboxyamino, (carboxy) (methyl)amino, (carboxy) (phenyl)amino, acetylamino, (acetyl) (methyl)amino, benzoylamino, (benzoyl) (methyl)amino, cyano, phenyl, sulphamoyl, methylsulphamoyl, dimethylsulphamoyl, phenylsulphamoyl, trifluoromethyl, 2,2,2-trifluoroethyl, 2-aminoethyl, 2-methylaminoethyl, 2-dimethylaminoethyl, 2-carboxyethyl, 2-sulphoethyl and oxo.

A particular value for the ring system formed when $R^9$ and $R^{10}$ are joined is a cyclobutene, cyclopentene, cyclohexene, cyclohexa-1,3-diene, cyclohexa-1,4-diene or benzene ring or a napththalene or dihydroacenaphthalene ring system.

A particular value for the optional substituent on the aromatic part of the ring system formed by $R^9$ and $R^{10}$ being joined is 1, 2 or 3 radicals selected from fluorine, chlorine, bromine, hydroxy, amino, cyano, carboxy, carbamoyl, nitro, ureido, methyl, ethyl, n-propyl, isopropyl, methoxy, ethoxy, isopropoxy, fluoromethyl, chloromethyl, trifluoromethyl, trichloromethyl, methylamino, ethylamino, hydroxymethyl, 1-hydroxyethyl, 2-hydroxyethyl, 3-hydroxypropyl, aminomethyl, 1-aminoethyl, 2-aminoethyl, 3-aminopropyl, acetylamino, propionylamino, azidomethyl, 2-azidoethyl, dimethylamino, diethylamino, acetylaminomethyl, methylaminomethyl, ethylaminomethyl, 1-methylaminoethyl, 2-methylaminoethyl, 1-ethylaminoethyl, 2-ethylaminoethyl, dimethylaminoethyl, diethylaminoethyl, 1-dimethylaminoethyl, 2-dimethylaminoethyl, 1-diethylaminoethyl, 2-diethylaminoethyl, cyanomethyl, 1-cyanoethyl, 2-cyanoethyl, carboxymethyl, 1-carboxyethyl, 2-carboxyethyl, carbamoylmethyl, 1-carbamoylethyl, 2-carbamoylethyl, ureidomethyl, 1-ureidoethyl, 2-ureidoethyl, a radical of the formula XVII, a radical of the formula XVIII, a radical of the formula XIX in which $R^{29}$, $R^{30}$, $R^{31}$ and $R^{32}$ are all hydrogen or one or more of $R^{29}$, $R^{30}$, $R^{31}$ and $R^{32}$ are methyl, a radical of the formula XX, a radical of the formula XXI and a radical of the formula XXII.

A particular value for $R^{11}$, $R^{12}$, $R^{13}$ or $R^{14}$ is hydrogen, cyano, carbamoyl, methoxycarbonyl, aminomethyl, 2-pyridyl, 3-pyridyl, 4-pyridyl, acetyl, propionyl, hydroxymethyl, 1-hydroxyethyl, 2-hydroxyethyl, 3-hydroxypropyl, methyl, ethyl, n-propyl, i-propyl, n-butyl, n-hexyl, phenoxymethyl, 1-phenoxyethyl, 2-phenoxyethyl, (diphenylmethyl)phenoxymethyl, phenyl, 2-, 3- or 4-fluorophenyl, 2-, 3- or 4-chlorophenyl, 2-, 3- or 4-bromophenyl, 2-, 3- or 4-cyanophenyl, 2-, 3- or 4-aminophenyl, 2-, 3- or 4-carboxyphenyl, 2-, 3- or 4-carbamoylphenyl, 2-, 3- or 4-hydroxyphenyl, 3,4-dihydroxyphenyl, 2-, 3- or 4-phenylphenyl, 2-, 3- or 4-phenoxyphenyl, 2-, 3- or 4-diphenylmethylphenyl, 2-, 3- or 4-methylaminophenyl, 2-, 3- or 4-acetylaminophenyl, 2-, 3- or 4-methanesulphonylaminophenyl, 2-, 3- or 4-aminomethylphenyl, 2-, 3- or 4-(2-aminoethyl)phenyl, 2-, 3- or 4-hydroxymethylphenyl, 2-, 3- or 4-dimethylaminophenyl, 2-, 3- or 4-diethylaminophenyl, 2-, 3- or 4-methoxycarbonylphenyl, 2-, 3- or 4-ethoxycarbonylphenyl, 2-, 3- or 4-methylcarbamoylphenyl, 2-, 3- or 4-ethylcarbamoylphenyl, 2-, 3- or 4-dimethylcarbamoylphenyl, or 2-, 3- or 4-diethylcarbamoylphenyl or $R^{12}$ and $R^{13}$, when in the cis relationship, are joined to form, together with the carbons to which they are attached, a cyclopropane, cyclobutane, cyclobutene, cyclopentane, cyclopentene, cyclohexane, cyclohex-3-ene, cyclohex-4-ene, 3-phenylcyclopropane, 3,3-diphenylcyclopropane, 3-trifluoromethylcyclopropane, 3,3-di(trifluoromethyl)cyclopropane, 3-phenyl-3-trifluoromethylcyclopropane, 3-phenylcyclobutane, 3,3-diphenylcyclobutane, 3,4-diphenylcyclobutane, 3-trifluoromethylcyclobutane, 3,3-di(trifluoromethyl)cyclobutane, 3,4-di(trifluoromethyl)cyclobutane, 3-phenylcyclobut-3-ene, 3,4-diphenylcyclobut-3-ene, 3-trifluorocyclobut-3-ene, 3,4-di(trifluoro)cyclobut-3-ene, 3-phenylcyclohexane, 3,3-diphenylcyclohexane, 3,4-diphenylcyclohexane, 3-trifluorocyclohexane or 3,4-ditrifluorocyclohexane ring, or $R^{11}$ is carboxy and $R^{12}$, $R^{13}$ and $R^{14}$ are hydrogen.

The following are nine preferred features of the cephalosporin derivative of the formula I. When any one of these features is taken, either singly or in combination, with the other general features of the cephalosporin derivative of the formula I listed above, there are obtained preferred sub groups of compounds within the above general definition.

1. $X^1$ is a sulphur atom.
2. The double bond to which S-$R^1$ is attached in trans.
3. $R^1$ is 1-methyltetrazol-5-yl.
4. $R^1$ is 5,6-dioxo-1,4,5,6-tetrahydro-1,2,4-triazin-3-yl substituted in the 4-position by formylmethyl.
5. $R^2$ is carboxy.
6. $R^3$ is hydrogen.
7. $X^2$ is nitrogen.
8. $R^4$ is hydrogen.
9. —A— is a radical of the formula V in which $R^9$ and $R^{10}$ are hydrogen.

The preferred compound of the invention is 7-(imidazol-2-yl)amino-3-[2-(1-methyltetrazol-5-ylthio)-trans-vinyl]ceph-3-em-4-carboxylic acid, and the pharmaceutically acceptable acid-addition salts and base-addition salts thereof.

A suitable acid-addition salt of the cephalosporin derivative of the invention is, for example, a salt formed with hydrochloric, hydrobromic, phosphoric, sulphuric, citric or maleic acid. A suitable base-addition salt of the cephalosporin derivative of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N$^1$-dibenzyl ethylenediamine, and other amines which have been used to form salts with cephalosporins).

The cephalosporin derivative of the formula I may be manufactured by methods known in themselves for the manufacture of chemically analogous compounds. The following processes, $R^1$, $R^2$, $R^3$, $R^4$, $X^1$, $X^2$ and —A— having the meanings stated above, unless indicated otherwise, are therefore provided as further features of the invention.

The process of the invention is characterised by:

(a) for those compounds in which $R^2$ is a carboxy radical or a heterocyclic radical carrying an acidic proton, and there is optionally a carboxy radical in another part of the molecule, deprotection of the corresponding compound which carries a protecting group, or groups, in place of the acidic hydrogen atom, or atoms. When $R^2$ is a carboxy radical a particularly useful protecting group is the diphenylmethyl or p-methoxybenzyl radical. Such a protecting group may be removed by treatment with a strong organic acid, for example trifluoroacetic acid. A further particularly useful protecting group is the t-butyl radical. This protecting group may be removed by treatment with a strong organic acid such as trifluoroacetic or formic acid. The process may be conducted in the presence of excess organic acid as diluent or solvent or in the presence of an additional diluent or solvent such as anisole or toluene. The process is preferably conducted at or below ambient temperature and preferably over a period of from 5 minutes to 5 hours. Other useful protecting groups are the trimethylsilyl radical (removed by water), the benzyl and substituted benzyl radicals, for example the p-nitrobenzyl or p-methoxybenzyl radical (removed by hydrogenolysis) and the 2,2,2-trichloroethyl radical (removed by zinc/acetic acid).

(b) reaction of a compound of the formula XXXVI:

[Formula XXXVI]

with a compound of the formula XXXVII:

[Formula XXXVII]

in which $R^{40}$ is a displaceable radical. $R^{40}$ is for example a halogen atom, preferably a fluorine or chlorine atom. The reaction is preferably conducted in the presence of at least one equivalent of an acid in order that the compound of the formula XXXVII is in the protonated form. The reaction may be conducted in the presence of a diluent or solvent, for example acetonitrile, dimethylformamide or tetrahydrofuran or mixtures of these and it may be accelerated or completed by the application of heat, for example by heating to 85° or to the boiling point of the diluent or solvent. When $X^2$ is a nitrogen atom and —A— is a radical of the formula V, the compound of the formula XXXVII may conveniently be prepared in situ by prior reaction of the corresponding N-triphenylmethyl derivative with toluene-p-sulphonic acid. The compound of the formula XXXVI is then added to the reaction mixture.

When the process of the invention manufactures the compound of the formula I in the form of the free acid or free base, or the zwitterion, and a salt is required, the compound of the formula I in the free acid or zwitterionic form is reacted with a base which affords a pharmaceutically-acceptable cation, or the compound of the formula I in the free base or zwitterionic form is reacted with an acid which affords a pharmaceutically-acceptable anion. When the process of the invention manufactures the compound of the formula I in the form of an acid-addition salt and the zwitterionic form is required, the compound of the formula I in the form of the acid-addition salt is reacted with a low molecular weight epoxide such as epoxypropane.

The starting material of the formula XXXVI for use in process (b) may be prepared by the general methods described in GB No. 2051061A, GB No. 2051062A, GB No. 2051788A and GB No. 2052488A followed, if necessary, by removal of the protecting group from the carboxylic acid at the 4-position. The starting material of the formula XXXVII for use in process (b) may be prepared by the general methods described in European Patent Publications Nos. 31708 and 55562.

The starting material for use in process (a) may be obtained by carrying out process (b) using a derivative of the compound of the formula XXXVI which carries a suitable protecting group or groups.

As noted above the cephalosporin derivative of the invention has antibacterial properties, having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system.

The antibacterial properties of the compounds of the invention may also be demonstrated in conventional mouse protection tests.

The results set out in the following Table of the compound described in the Example are illustrative of the biological activity of the compounds of the present invention. The results are those obtained on a standard in vitro test system using Jewell and Pearmain agar medium. The antibacterial activity is described in terms of the minimum inhibitory concentration (MIC) determined by agar-dilution technique with an inoculum size of $\sim 10^5$ CFU.

| Organism | Code No. | MIC μg/ml |
|---|---|---|
| Strep. pyrogenes | A1 | 1 |
| Staph. aureus | A6 | 8 |
| E. coli | A8 | 0.12 |
| Salmonella dublin | A20 | 0.12 |
| K. aerogenes | A10 | 2 |
| Ent. cloacae | A13 | 32 |
| Serratia marescens | A16 | >128 |
| Proteus mirabilis | A18 | 32 |
| Ps. aeruginosa | A21 | >128 |

According to a further feature of the invention there is provided a pharmaceutical composition which comprises a cephalosporin derivative of the invention in association with a non-toxic pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents, (for example other β-lactams or aminoglycosides), inhibitors of β-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Example. The n.m.r. spectra are quoted in δ relative to tetramethylsilane (δ=0) as internal standard, (s=singlet, d=doublet, t=triplet, m=multiplet, br=broad). The temperatures are in degrees Centigrade. The following contraction is used:

DMSO=dimethylsulphoxide

EXAMPLE

A solution of the hydrochloried/hydrofluoride salt of diphenylmethyl 7-(imidazol-2-yl)amino-3-[2-(1-methyl-tetrazol-5-ylthio)-trans-vinyl]ceph-3-em-4-carboxylate (300 mg.) in a mixture of water (2 ml.) and formic acid (2 ml.) was heated to 40°-45° for 1.75 hours. The solvent was evaporated and the residue dissolved in the minium amount of a mixture of $CH_2Cl_2$, methanol and water. Precipitation by addition of isopropanol gave 7-(imidazol-2-yl)amino-3-[2-(1-methyltetrazol-5-ylthio)-trans-vinyl]ceph-3-em-4-carboxylic acid as a salt (73 mg.) having the following n.m.r. in $d_6DMSO+CD_3COOD$: 3.62 (m, 2H); 3.90 (s, 3H); 5.1 (d, 1H); 5.5 (d, 1H); 6.7 (d, 1H); 7.2 (d, 1H); 6.75 (s, 2H).

The starting material may be obtained as follows:

A mixture of diphenylmethyl 7-amino-3-[2-(1-methyltetrazol-5-ylthio)-trans-vinyl]ceph-3-em-4-carboxylate (520 mg.) and 2-fluoroimidazole hydrochloride (237 mg; 4 equivalents) was heated at 65°-70° for 4 hours in dimethylformamide (4 ml.). A portion of 2-fluoroimidazole as the free base (2 equivalents) was then added and heating was continued for 2 hours. The solvent was evaporated under reduced pressure and the residue purified by chromatography on silica gel using $CH_2Cl_2$/methanol/acetic acid 90:8:2 v/v/v as eluant. There was thus obtained diphenylmethyl 7-(imidazol-2-yl)amino-3-[2-(1-methyltetrazol-5-ylthio)-trans-vinyl]ceph-3-em-4-carboxylate as the mixed hydrochloride/hydrofluoride salt (306 mg.) having the following n.m.r. in $d_6DMSO$: 3.6 (m, 2H); 3.92 (s, 3H); 5.12 (d, 1H); 5.7 (m, 1H); 6.6 (s, 2H); 7.2 (s, 1H); 7.32 (m, 12H).

We claim:
1. A cephalosporin derivative of the formula I:

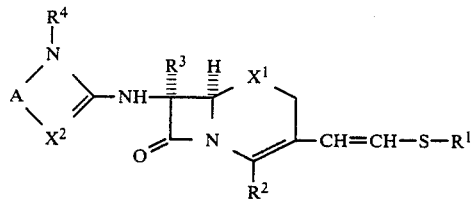

in which $X^1$ is sulphur; $R^1$ is
(1) pyridazin-3-yl substituted in the 6-position by 1-6C alkyl, methoxy, amino or 1-6C alkanoylamino, or the N-oxide thereof, or pyrimidin-2-yl or tetrazolo[4,5-b]-pyridazin-6-yl;
(2) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl in which the alkoxycarbonyl is 2-6C, each substituted in the 1-position:
(a) by 1-6C alkyl, unsubstituted or substituted by 1-6C alkoxy, 1-6C alkylthio, phenyl, formyl, carbamoyl, 2-6C alkylcarbamoyl, 3-10C dialkylcarbamoyl, 1-6C alkanoyl, 2-6C alkoxycarbonyl or thiazolidin-2-yl;
(b) by allyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxyprop-2-yl;
(c) by 2-4C alkyl substituted by hydroxy, carbamoyloxy, 1-6C alkanoyl (which can itself be optionally substituted by amino, 1-6C alkylamino or 2-10C dialkylamino), 1-6C alkanesulphinyl, 1-6C alkanesulphonyl, amino, 1-6C alkylamino, 2-10C dialkylamino, sulphoamino, 1-6C alkanesulphonylamino, sulphamoylamino, 1-6C alkanoylamino which is unsubstituted or which can itself be substituted by hydroxy, amino, 1-6C alkylamino or 2-10C dialkylamino), 2-6C alkoxycarbonylamino, ureido, 2-6C alkylureido, or 3-10C dialkylureido;
(d) by a radical of the formula II, III or IV:

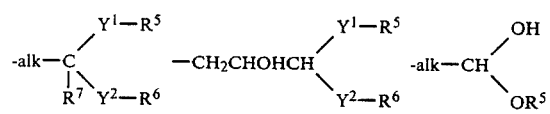

II          III          IV in which alk is 1-4C alkylene, $Y^1$ and $Y^2$ are the same and are oxygen or sulphur and $R^5$ and $R^6$ are the same and are 1-6C alkyl, or $Y^1$ and $Y^2$ are the same or different and are oxygen or sulphur and $R^5$ and $R^6$ are joined to form 2-3C alkylene, and $R^7$ is hydrogen or 1-3C alkyl;
(e) by 1-6C alkyl substituted by 1-6C alkoxyimino or hydroxyimino;
(3) 1,4-dialkyl-5,6-dioxo-1,4,5,6-tetrahydro-hydro-1,2,4-triazin-3-yl, 1-alkyl-5,6-dioxo-1,4,5,6-tetratetrahydro-1,2,4-triazin-3-yl in each of which the alkyl is 1-6C;

(4) 1,3,4-triazol-5-yl, 1,2,3-triazol-5-yl or 1-alkyl-1,2,3-triazol-5-yl in which the alkyl is 1-6C which is unsubstituted or substituted in the 3-position by 2-6C alkoxycarbonyl;

(5) a. 1,3,4-thiadiazol-5-yl which is unsubstituted or substituted by 1-6C alkyl, trifluoromethyl, 1-6C alkoxy, 1-6C alkylthi, 2-4C hydroxyalkylthio, 1-6C alkanesulphonyl hydroxy, 1-6C hydroxyalkyl, carboxy, 2-6C carboxyalkyl, amino, 1-6C alkylamino, 2010C dialkylamino, 1-6C aminoalkyl, 2-8C alkylaminoalkyl, 3-12C dialkylamino-alkyl, 1-6C alkanoylamino or 2-8C alkanoylamino-alkyl, or b. 1,2,4-thiadiazol-5-yl substituted by 1-6C alkyl or 1-6C alkoxy;

(6) a. 1,3,4-oxadiazol-5-yl which is unsubstituted or substituted by 1-6C alkyl, trifluoromethyl, phenyl, 1-6C aminoalkyl, 2-8C alkylaminoalkyl, 3-10C dialkylaminoalkyl or 2-8C alkanoylaminoalkyl or b. oxazol-2-yl which is unsubstituted or substituted in the 4-position by 1-6C alkyl;

(7) tetrazol-5-yl which is unsubstituted or substituted in the 1-position by:
(a) 1-6C alkyl which is unsubstituted or substituted by 1-6C alkoxy, sulpho, carboxy, formyl or sulphamoyl;
(b) 2-4C alkyl substituted by hydroxy, amino, 1-6C alkylamino, 2-8C dialkylamino, 1-6C alkanoylamino, 2-6 carboxyalkylamino, sulphamoylamino, sulphoamino, ureido, 206C alkylureido or 3-8C dialkylureido;
(c) 1-5C alkyl substituted by hydroxyimino or 1-6C alkoxyimino;
(d) phenyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxy-2-propyl; or
(e) a radical of the formula II above in which R⁷ is hydrogen, or a radical of the formula III above, in both of which Y¹, Y², R⁵ and R⁶ are as given above;

R² is a carboxy radical; X² is nitrogen; R³ is hydrogen; R⁴ is hydrogen and —A— is a radical of the formula V:

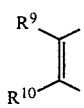

in which R⁹ and R¹⁰ are hydrogen and the pharmaceutically-acceptable acid- or base-addition salts thereof.

2. A cephalosporin derivative as claimed in claim 1 in which R¹ is 1-methyltetrazol-5-yl or 5,6-dioxo-1,4,5,6-tetrahydro-1,2,4-triazin-3-yl substituted in the 4-position by formylmethyl.

3. The compound 7-(imidazol-2-yl)amino-3-[2-(1-methyltetrazol-5-ylthio)-trans-vinyl]ceph-3-em-4-carboxylic acid and the pharmaceutically-acceptable acid-addition and base-addition salts thereof.

4. A pharmaceutical composition for treating bacterial infection which comprises an antibacterially-effective amount of a cephalosporin derivative as claimed in claim 1 in association with a pharmaceutically-acceptable diluent or carrier.

5. A method of treating a bacterial infection in a warm-blooded animal which comprises administering to the animal a therapeutically-effective amount of the compound of claim 1.

6. A cephalosporin derivative of the formula I:

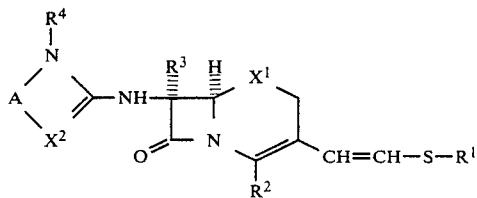

in which X¹ is sulphur; R¹ is
(1) pyridazin-3-yl substituted in the 6-position by methyl, methoxy, amino or acetylamino, or the N-oxide thereof, or pyrimidin-2-yl or tetrazolo[4,5-b]pyridazin-6-yl;
(2) 5,6-dioxo-1,4,5,6-tetrahydro-1,2,4-triazin-3-yl substituted in the 4-position; 1,3,4-triazol-5-yl or 2-methoxycarbonyl-1,3,4-triazol-5-yl, each substituted in the 1-position:
(a) by methyl which is unsubstituted or substituted by methoxy, methylthio, phenyl, formyl, carbamoyl, methyl-carbamoyl, dimethylcarbamoyl, acetyl, methoxycarbonyl or thiazolidin-2-yl;
(b) by allyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bis-formyloxyprop-2-yl;
(c) by ethyl substituted by hydroxy, carbamoyloxy, acetyl (which is itself unsubstituted or substituted by amino, methylamino, or dimethylamino), methanesulphinyl, methanesulphonyl, amino, methylamino, dimethylamino, sulphoamino, methanesulphonylamino, sulphamoylamino, acetylamino (which is itself unsubstituted or substituted by hydroxy, amino, methylamino or dimethylamino), methoxycarbonylamino, ureido, methylureido, or dimethylureido;
(d) by a radical of the formula II, III or IV:

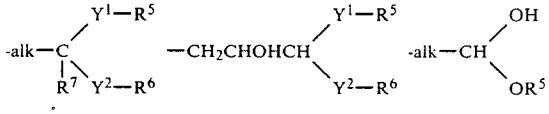

II    III    IV in which alk is methylene, Y¹ and Y² are the same and are oxygen or sulphur and R⁵ and R⁶ are the same and are methyl, or Y¹ and Y² are the same or different and are oxygen or sulphur and R⁵ and R⁶ are joined to form ethylene, and R⁷ is hydrogen or methyl;
(e) by methyl substituted by methoxyimino or hydroxyimino;
(3) 1,4-dimethyl-5,6-dioxo-1,4,5,6-tetrahydro-hydro-1,2,4-triazin-3-yl, 1-methyl-5,6-dioxo-1,4,5,6-tetra-tetrahydro-1,2,4-triazin-3-yl;

(4) 1,3,4-triazol-5-yl, 1,2,3-triazol-5-yl or 1-methyl-1,2,4-triazol-5-yl which is unsubstituted or substituted in the 3-position by methoxycarbonyl;
(5) a. 1,3,4-thiadiazol-5-yl which is unsubstituted or substituted by methyl, trifluoromethyl, methoxy, methylthio, 2-hydroxyethylthio, methanesulphonyl, hydroxy, hydroxymethyl, carboxy, carboxymethyl, amino, methylamino, dimethylamino, aminomethyl, methylaminomethyl, dimethylaminomethyl, acetylamino or acetylaminomethyl, or
b. 1,2,4-thiadiazol-5-yl substituted by methyl or methoxy;
(6) a. 1,3,4-oxadiazol-5-yl which is unsubstituted or substituted by methyl, trifluoromethyl, phenyl, aminomethyl, methylaminomethyl, dimethylaminomethyl or acetylaminomethyl or
b. oxazol-2-yl which is unsubstituted or substituted in the 4-position by methyl;
(7) tetrazol-5-yl which is unsubstituted or substituted in the 1-position by:
  (a) methyl which is unsubstituted or substituted by methoxy, sulpho, carboxy, formyl or sulphamoyl;
  (b) ethyl substituted by hydroxy, amino, methylamino, dimethylamino, acetylamino, carboxymethylamino, sulphamoylamino, sulphoamino, ureido, methylureido or dimethylureido);
(c) methyl) substituted by hydroxyimino or methoxyimino;
(d) phenyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxy-2-propyl; or
(e) a radical of the formula II above in which $R^7$ is hydrogen, or a radical of the formula III above, in both of which $Y^1$, $Y^2$, $R^5$ and $R^6$ are as given above;
$R^2$ is carboxy,
$R^3$ is hydrogen;
$X^2$ is nitrogen;
$R^4$ is hydrogen and
—A— is a radical of the formula V

V in which $R^9$ and $R^{10}$ are hydrogen and the pharmaceutically-acceptable acid- or base-addition salts thereof.

* * * * *